(12) United States Patent
Armstrong et al.

(10) Patent No.: US 7,052,863 B2
(45) Date of Patent: May 30, 2006

(54) ALIZARIN-BASED CHROMOGENIC SUBSTRATES, THEIR USES AND COMPOSITION CONTAINING SAME

(75) Inventors: Lyle Armstrong, East Ashington (GB); Arthur James, Newcastle Upon Tyne (GB)

(73) Assignee: Biomerieux S. A., Marcy L'Etoile (FR)

( * ) Notice: Subject to any disclaimer, the term of this patent is extended or adjusted under 35 U.S.C. 154(b) by 368 days.

(21) Appl. No.: 10/148,600

(22) PCT Filed: Dec. 11, 2000

(86) PCT No.: PCT/FR00/03465

§ 371 (c)(1),
(2), (4) Date: Jun. 3, 2002

(87) PCT Pub. No.: WO01/42490

PCT Pub. Date: Jun. 14, 2001

(65) Prior Publication Data

US 2003/0082667 A1    May 1, 2003

(30) Foreign Application Priority Data

Dec. 9, 1999    (FR) .................................. 99 15515

(51) Int. Cl.
*C12Q 1/37* (2006.01)
*C07H 15/24* (2006.01)
*C07H 21/04* (2006.01)
*C07D 211/06* (2006.01)
*C09B 1/00* (2006.01)

(52) U.S. Cl. ........................ 435/23; 530/406; 536/18.1; 536/23.1; 544/155; 546/204; 548/528; 552/238

(58) Field of Classification Search .................... 435/4, 435/7.35, 18, 29, 34, 38, 39, 252.8, 23; 536/4.1, 536/18.1; 530/406
See application file for complete search history.

(56) References Cited

U.S. PATENT DOCUMENTS 4,366,241 A * 12/1982 Tom et al. .................. 435/7.91
6,146,840 A * 11/2000 Chang et al. .................. 435/14

OTHER PUBLICATIONS

Palmer, Carol, J. et al. Applied and Environmental Microbiology, 1993, vol. 59, pp. 786-790.*
Clark, James, A. et al. Applied and Environmental Microbiology, 1993, vol. 59, pp. 380-388.*
Brown et al. 1979.Mutation Research. vol. 66, pp. 9-24.*
Masawaki et al., "Selective Solvent Extraction of Ruberythric Acid From Madder Roots and Subsequent Hydrolysis With β-Glucosidase," 81 *J. Fermentation and Bioengineering* 567-569 (1996).
Van der Plas et al., "Anthraquinone Glycosylation and Hydrolysis In Morinda Citrifolia Cell Suspensions: Regulation and Function," 152 *J.Plant Physiology* 235-241 (1998).
Mateju et al., "Microbial Glucosidation of Dihydroxyanthraquinones. General Properties of the Glucosidation System," 19 *Folia Microbiol.* 307-316 (1974).
James et al., "Alizarin β-D-galactoside: A New Substrate for the Detection of Bacterial β-galactosidase ," 30 *Letters in Applied Microbiology* 336-340 (2000).

* cited by examiner

*Primary Examiner*—Ralph Gitomer
*Assistant Examiner*—Kailash C. Srivastava
(74) *Attorney, Agent, or Firm*—James C. Lydon

(57) ABSTRACT

An alizarin-based chromogenic substrate, a composition containing the substrate, and its use to detect the presence of an enzymatic activity are disclosed. The substrate is particularly applicable in the field of biological diagnosis.

14 Claims, No Drawings

ALIZARIN-BASED CHROMOGENIC SUBSTRATES, THEIR USES AND COMPOSITION CONTAINING SAME

This application is a U.S. National Stage of International application PCT/FR00/03465, filed Dec. 11, 2000, and published on Jun. 14, 2001 in the French Language.

This invention concerns the detection of hydrolytic enzymes, in particular saccharidases, esterases and peptidases, by means of the use of effective chromogenic substrates.

For many years, special substrates have been used to determine whether enzymatic activities typical of microorganisms are present or not. Through the use of specific substrates, it is possible—on the basis of whether a reaction takes place or not—to characterize the nature of a genus of microorgansms, or distinguish between different strains and/or species belonging to a given genus.

Synthetic enzyme substrates are made up of two different parts: the first part is specific to the enzyme activity being tested for and will hereafter be referred to as the target part; the second part acts as a marker and will hereafter be referred to as the marker part.

Such special substrates may be either fluorescent or chromogenic. In fact, the second marker part or the product of its reaction with one or more other compounds becomes fluorescent or chromogenic when it is no longer associated with the first target part (in this context, refer to Patent Application PCT/FR99/00781 filed on behalf of the applicant).

This invention concerns chromogenic substrates based on the Alizarins or Anthrarobins which, when incorporated into a substrate form usually have some coloration. However, the color due to the marker part becomes accentuated and/or altered following hydrolysis which leads to the separation of said marker part from the target part of the substrate. Preferably, the color properties of the product generated are further enhanced by virtue of the presence of a developer factor (e.g. a metal salt or high pH).

The capacity of the Alizarins to form colored chelation complexes with metals was discovered in the Nineteenth Century. Beginning in 1826 when Alizarins were first isolated from the plant *Rubia tinctorum*, their properties as dyes were exploited in tinting fabrics.

A complete synthetic pathway for the Alizarins was developed by Graebe and Liebermann in 1869. In the same year, W. H. Perkin extended the number of different Alizarins which could be synthesized by substituting different groups at positions $R_3$, $R_4$, $R_5$, $R_6$, $R_7$ and $R_8$ of the anthracene nucleus (shown below):

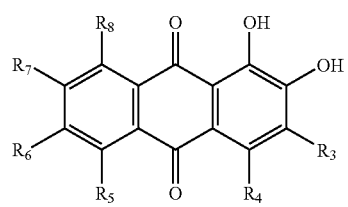

The Alizarins are not in themselves dyes but rather form insoluble pigments with metal oxides. For example, when a sulfone group is substituted in at position $R_3$, chelation with an Aluminum salt gives rise to a bright scarlet-red color whereas chelation with a chromium salt gives a Bordeaux-like shade of Red. Taking another example, 3-Nitroalizarin and 4-Nitroalizarin give complexes of different colors according to the metal salts with which they are chelated.

The usefulness of the Alizarins in the dying industry is largely due to the stability of the chelation complexes they form with metals, be they in the form of soaps, acids or the hydroxides of alkali metals.

Among the Alizarin derivatives which are easy to synthesize, it can be noted that 3-Aminoalizarin and 4-Aminoalizarin can be generated from 3-Nitroalizarin and 4-Nitroalizarin. 4-Aminoalizarin is represented below:

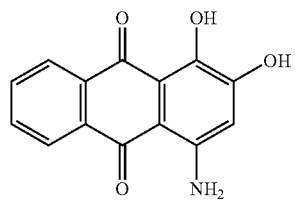

This compound is of particular interest because it gives a purple color in the presence of aluminum. Moreover, it is the starting point for the synthesis—using a Skraup reaction which is familiar to those skilled in the art—of the quinoline Alizarins, one of which, Alizarin a-quinoline (which is green) is represented below:

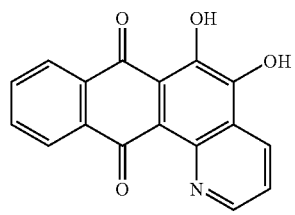

Substitution and ring-closure reactions make it possible to generate a whole series of modified A lizarins with differing properties.

The prior art also shows that these compounds already have biological and biomedical applications. Because of the speed with which Hydroxyanthraquinones react in the presence of chelation complexes, they have found a preferred application in tests to detect whether metals are present or not in biological specimens.

The anthrarobins (also referred to as Deoxyalizarin or Anthracene-1,2,10-triol) which are produced by the reduction of Alizarins, are already familiar to those skilled in the art. Reduction is mediated by the action of Zinc hydroxide, ammonia, acid tin chloride, etc. This compound's general formula is as follows:

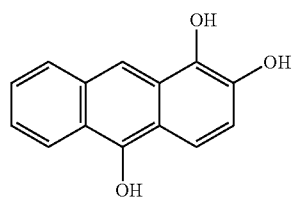

However, up till now, no reference has been made to one particular area in which Alizarins, Anthraquinoid derivatives and Anthrarobins find applications, namely in the detection of enzyme activity. This necessarily involves the synthesis of substrates in which at least one target part is conjugated with the Alizarin molecule. These substrates have the advantage that they fail to react in the presence of metal ions as long as no hydrolysis reaction has occurred to separate the two different parts. The fact that the chelation complexes formed are insoluble results in a number of significant advantages:

- enhanced sensitivity, even at a low concentration, meaning that only a small amount of substrate needs to be used,
- the color of the hydrolysis product can be readily adapted to the requirements of the particular application by modifying the composition of the reaction medium, notably the levels of polyvalent cations (a definition of which will be given in the special points at the end of this description) it contains and/or its pH.
- they are easy to synthesize and a only a small amount of substrate is needed (by virtue of the great sensitivity mentioned above), both of which factors reduce production costs,
- the colored product diffuses inefficiently so that colonies are easy to resolve and distinguish, and
- growth is relatively uninhibited since such only trace amounts of substrate are necessary (by virtue of the great sensitivity mentioned above).

Alizarin derivatives have been synthesized, mainly bound to glycosides, using a fairly classic pathway referred to as the Koenigs-Knorr method (Koenigs, W. and Knorr, E., Ber., 34, 957, 1901). α-glycosides are synthesized using a modified version of the Helferich method (Helferich B. et al., Ber., 66, 378 (1933) and Ber., 77, 194 (1944). Other derivatives are bound to short-chain fatty acids and esters of phosphoric or sulfuric acid.

Hitherto, the substrates used have been, e.g. 5-Bromo-4-chloro-3-indolyl-β-D-galactoside which will be dealt with later in a comparative analysis with one of the substrates according to the invention, namely Alizarin-β-D-galactoside.

In accordance with this invention, the substrates according to the invention are substantially more effective than those covered in the prior art. Thus, they detect a greater number of species and/or strains of microorganism for any specific enzyme activity being assayed.

The substrates according to the invention are mentioned to varying extents in other documents.

Thus, an article by Masawaki. Teruyuki et al., "Selective solvent extraction of ruberythric acid from madder roots and subsequent hydrolysis with β-glucosidase", J. Ferment. Bioeng. (1996), 81(6), 567–569, concerns a process for the extraction of anthraquinones—to be used as dyes—from madder roots, based on the use of a selective solvent. One of the aims was to extract Alizarins from Anthraquinones bound to sugars; one such species was Alizarin-2-o-primeveroside. In order to achieve this, they hydrolyzed Alizarin-2-o-primeveroside using β-glucosidase.

Another article published by Van der Plas, Linus H. W. et al. "Anthraquinone glycosylation and hydrolysis in Morinda citrifolia cell suspensions. Regulation and function", J. Plant. Physiol., (1998), 152(2/3), 235–241, proposes a biological explanation for the presence of a sugar-the glycosylated Primeveroside—in plant cells (see page 240 column 1, paragraph 3). According to this, it is generated by the hydrolysis of certain Anthraquinones.

A final article published by Mateiu, J et al. "Microbial glucosidation of dihydroxyanthraquinones. General properties of the glucosidation system", Folia Microbiol. (Prague) (1974), 19(4), 307–316 concerns the "glucosidation" activity of the B96 mutant strain of Streptomyces aureofaciens.

However, these are only distantly related to the Applicant's invention. Although it is true that all three mention substrates based on Alizarin (or other anthraquinones), their diversity is restricted (with mention of only a few compounds), and all are generated by biological pathways (substrates combining a Primeveroside and produced by plants in the first two articles; substrates combining various glucosides and produced by the bacterium Streptomyces griseus in the third). Moreover, these substrates are not used to develop diagnostic tests based on the detection of enzymes.

To this effect, this invention concerns a chromogenic substrate to detect the presence of an enzyme activity, with the following general formula:

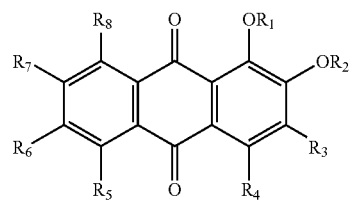

in which:
$R_1$ is a target part or H, and $R_2$ is a target part or H, with at least one out of $R_1$ and $R_2$ being a target part,
$R_3$ is H, $SO_3H$, Cl, Br, F, I, $NO_2$, $NH_2$, $NR_9R_{10}$, or an Acylamino Aminoaryl or Aminoacylamino group of the type NHCOX, with X being an Alkyl, Aryl or Aralkyl group or an α-amino acid residue such as Alanine,
R4 is H, $SO_3H$, Cl, Br, F, I, $NO_2$, $NH_2$, $NR_9R_{10}$, OH or an Acylamino Aminoaryl or Aminoacylamino group of the type NHCOX, with X being an Alkyl, Aryl or Aralkyl group or an α-amino acid residue such as Alanine,
according to a modification, $R_3$ and $R_4$ form bonds with one another to create a ring with at least five sides, and preferably six sides.
$R_5$, $R_6$, $R_7$ and $R_8$ each consist of one of the following atoms or groups of atoms: H, a halogen (particularly Cl or Br), OH, $SO_3H$, or an Alkyl or Alkoxy group, and
$R_9$ a $R_{10}$ are independently a Methyl, Alkyl, Aryl, Aralkyl group, or one (either $R_9$ or $R_{10}$) is a ring structure (Piperidine, Pyrrolidine, Morpholine, etc.) with the other (either $R_{10}$ or $R_9$) being a Hydrogen atom.

In a special case, the ketone groups of the central ring are reduced to form hydroxide groups in which at least one of the hydrogen atoms might be replaced by a Methyl, Alkyl, Aryl or Aralkyl group.

This invention also concerns a chromogenic substrate to detect the presence of an enzyme activity, with the following general formula:

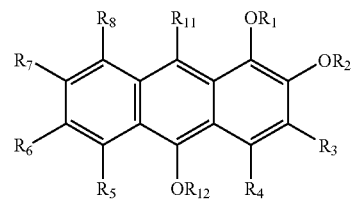

in which:
$R_1$ is a target part or H, and $R_2$ is a target part or H, with at least one out of $R_1$ and $R_2$ being a target part,
$R_3$ is H, $SO_3H$, Cl, Br, F, I, $NO_2$, $NH_2$, $Nr_9R_{10}$, or an Acylamino Aminoaryl or Aminoacylamino group of the type NHCOX, with X being an Alkyl, Aryl or Aralkyl group or an α-amino acid residue such as Alanine, R4 is H, $SO_3H$, Cl, Br, F, I, $NO_2$, $NH_2$, $NR_9R_{10}$, OH or an Acylamino Aminoaryl or Aminoacylamino group of the type NHCOX, with X being an Alkyl, Aryl or Aralkyl group or an α-amino acid residue such as Alanine, according to a modification, $R_3$ and $R_4$ form bonds with one another to create a ring with at least five sides, and preferably six sides.

$R_5$, $R_6$, $R_7$ and $R_8$ each consist of one of the following atoms or groups of atoms: H, a halogen (particularly Cl or Br), OH, $SO_3H$, or an Alkyl or Alkoxy group, and $R_9$ a $R_{10}$ are independently a Methyl, Alkyl, Aryl, Aralkyl group, or one (either $R_9$ or $R_{10}$) is a ring structure (Piperidine, Pyrrolidine, Morpholine, etc.) with the other (either $R_{10}$ or $R_9$) being a Hydrogen atom.

$R_{11}$, consists of one of the following atoms or groups of atoms: H, $SO_3H$, Cl, Br, F, I, $NO_2$, $NH_2$, $NR_9R_{10}$, or an Alkyl, Aryl, Aralkyl, Acylamino Aminoaryl or Aminoacylamino group of the type NHCOX, with X being an Alkyl, Aryl or Aralkyl group or an α-amino acid residue, and $R_{12}$ consists of H, or a Methyl, Alkyl, Aryl or Aralkyl group.

In a special case in which one of the above-mentioned substrates is hydrolyzed, the marker part consists of an Alizarin which is carrying two hydroxyl groups at positions 1 and 2. The name of this compound is 1,2-Dihydroxyanthraquinone-β-D-galactoside and its general formula, when it is conjugated with a target part consisting of galactose, is:

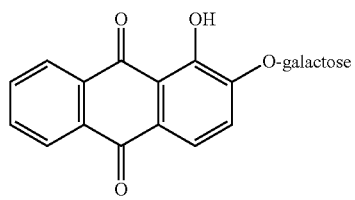

The product generated when this compound is hydrolyzed by a β-galactosidase forms the following chelation complex in the presence of an iron salt:

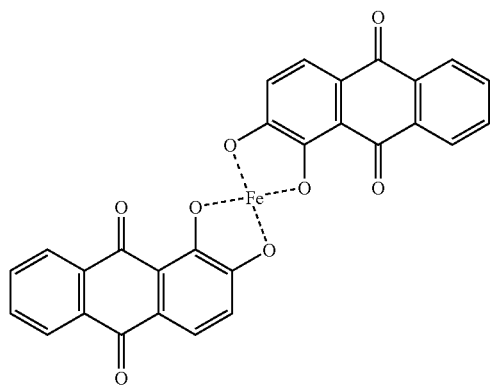

In all the examples given above, $R_1$ is preferably H and $R_2$ is preferably the target part.

More precisely, the target part consists of one of the following species:

a Glycoside, consisting of mono-, di- or poly-saccharide sub-units, joined to the hydroxyl group through an α or β linkage, an α-amino acid or a peptide, an organic acid, such as —O—CO—$(CH_2)_n$—$CH_3$, in which n has a value of between 0 and 20, or Sulfate, Phosphate, Pyrosulfate, Pyrophosphate or Phosphodiester.

In a special case, $R_3$ and $R_4$ are such that, when joined to one another through a $C_3N$ chain (which might or might not be substituted) with the N preferably adjacent to $R_3$ or $R_4$, a six-sided ring is formed.

According to a first embodiment of at least one substrate as described above for the detection of an enzyme activity, the use consists in:

bringing at least one substrate, the target part of which matches the activity of the enzyme being assayed, into contact with a sample suspected of containing at least one microorganism which expresses the enzyme activity in question, and at least one type of cation, and monitoring for the formation of an insoluble, colored chelation complex.

Preferably, the substrate is introduced into the presence of at least one type of cation which is appropriate for the marker part released by the enzyme activity.

Still preferably, the type of cation which can be used to form insoluble chelation complexes consists of. $Fe^{2+}$, $Al^{3+}$, $Mn^{2+}$, $Sn^{2+}$ or $Cu^{2+}$.

If at least two substrates are being used, as described above, in order to make it possible to detect at least two different enzyme activities, the use consists in:

bringing at least two substrates, the target parts of which match the activities of the two (at least) enzymes being assayed, into contact with a sample suspected of containing at least one microorganism which expresses the enzyme activities in question, plus at least one type of cation, and monitoring for the development of at least two different colors or a third color.

According to the last case, the substrates are introduced into the presence of at least one type of cation, preferably a single type of cation, which is appropriate for the marker parts released by the enzyme activities.

In all the examples, the use of at least one substrate as described above to detect the presence of an enzyme activity, or this use in parallel with a use already described previously, consists in:

bringing at least one substrate, the target part of which matches the activity of the enzyme being assayed, into contact with a sample suspected of containing at least one microorganism which expresses the enzyme activity in question, in a reaction medium with an appropriate pH, and monitoring for the development of at least one color.

Preferably, when at least two substrates are being used, only one single type of cation should be used, this cation being appropriate for all the marker parts released by the enzyme activities.

According to a preferred embodiment, the above-mentioned uses include an intermediate step consisting in allowing the microorganism(s) to grow in or on a medium which has been supplemented with the substrates.

If it is glycosidase activity which is to be detected, the target part used could be (among other possibilities):

Glucose,
Galactose,
Mannose,
Xylose,

Glucuronic acid, or

N-acetylglucosamine.

If it is phosphatase activity which is to be detected, the target part used could be (among other possibilities) Phosphoric acid or a substituted derivative thereof If it is sulfatase activity which is to be detected, the target part used could be (among other possibilities) Sulfuric acid or a substituted derivative thereof If it is lipase, phospholipase or esterase activity which is to be detected, the target part used could be (among other possibilities):

A fatty acid (saturated or non-saturated), or a substituted derivative thereof,

Acetic acid, or a substituted derivative thereof,

Butyric acid, or a substituted derivative thereof,

Octanoic acid, or a substituted derivative thereof, or

An esterified phosphate group such as inositol-1-phosphate.

The invention also concerns a formulation for the detection of at least one strain and/or species of microorganism which includes at least one substrate as described above plus a culture medium.

If the formulation contains at least two substrates, the reaction products formed should have different colors so that distinction can be made between the different enzyme activities expressed by at least one strain and/or species of microorganism.

Preferably, the form in which the formulation is presented is liquid, semi-solid or solid (e.g. a dry form ready for resuspension in an appropriate solution).

Still preferably, the substrate is at a concentration of between 10 and 500 mg/l, preferably between 30 and 150 mg/l, and more preferably still, 50 mg/l.

Therefore, this invention concerns a novel substrate which, at first faintly colored, takes on a more marked color in the presence of, on the one hand a microorganism or an enzyme, the presence of which it is desired to detect, and on the other hand (in some cases) a cation. The invention also concerns the uses to which such a substrate can be put, and a formulation containing this substrate.

Having cations present is particularly useful, although not absolutely neessary; in the latter case, the formulation used would preferably have an alkaline pH. It is also possible to combine both of these conditions, i.e. the presence of a cation plus alkaline pH.

When different cations are used, the colonies of the microorganisms being tested take on different colors. Cations such as Iron, Manganese, Tin and Aluminum are used at very low concentrations in order to prevent or minimize the inhibition of growth caused by free ions in the test specimen.

However, high concentrations of certain metal ions induce selective inhibition which may be exploited to select particular microbial species, thus constituting an additional advantage.

SUBSTRATE SYNTHESIS

1°) Synthesis of Alizarin-2-β-D-glucoside

According to Robertson et al., (J. Chem. Soc. (1930), 1136 et (1933), 1167), Alizarin is specifically glycosylated at the hydroxyl group in position 2, although this addition can be made at position 1. Nevertheless, conjugation at position 2 is easier.

This substrate was prepared using a modified version of the method described by Robertson (1933). A mass of 6 g of Alizarin was resuspended in 70 ml of acetone and mixed with 70 ml of Potassium hydroxide solution (0.28 mol/l) in order to form a salt. Added to this was a mixture of 40 ml of a 1:1 mixture of Ether and Acetone containing 6.6 g of Aceto-bromo-glucose. The mixture was stirred for about 14 hours. Then, 7 ml of Potassium hydroxide solution (1.25 mol/l) were added, followed by 15 ml of Aceto-bromo-glucose (0.6 mol/l) in Acetone. The premixture was stirred for a further ten hours. The Ether and the Acetone were evaporated off at low pressure and the pH was adjusted to about 5.5 using glacial Acetic acid. The mixture containing some unreacted Alizarin was filtered and then washed in water before being dried overnight at 50° C.

The resultant yellow solid was resuspended in 70 ml of glacial Acetic acid and ///shaken therein for 5 minutes. This cooled it down prior to filtration after which it was washed in Acetic acid. The filtrate was then left for one hour and separated from any residual Alizarin. This procedure was then repeated at 10° C. to yield a dark green filtrate.

The product was dried and dissolved in 200 ml of Dichloromethane before the addition of 2 ml of Triethylamine. An Aluminum oxide was premixed into the solution until thin layer chromatography (TLC) of test samples showed that no Alizarin remained. The Aluminum oxide was removed and the remaining solution was evaporated with rotary motion, yielding a yellow solid. This solid was recrystallized from hot Ethanol which contained a few drops of Acetic acid. This gave 2.02 g of Alizarin Tetra-acetyl-glucoside.

A mass of 1.1 g of Alizarin Tetra-acetyl-glucoside was resuspended in 60 ml of Ethanol before the addition of 30 ml of aqueous Sodium hydroxide (0.125 mol/l) to give a red solution. This mixture was kept at 65° C. for 10 minutes and then cooled to 0° C. The red glycosylated Alizarin Sodium salt was then removed by vacuum filtration, washed with Ether and finally dried. The procedure yielded 0.9 g of the Sodium salt of Alizarin-2-β-D-glucoside. This product can be further purified using techniques familiar to those skilled in the art to yield Alizarin-2-β-D-glucoside.

2°) Synthesis of Alizarin-2-β-D-galactoside

This substrate was also prepared using a modified version of the method described by Robertson (1933). A mass of 6 g of Alizarin was resuspended in 70 ml of acetone and mixed with 70 ml of Potassium hydroxide solution (0.28 mol/l) in order to form a salt. Added to this was a mixture of 40 ml of a 1:1 mixture of Ether and Acetone containing 6.6 g of Aceto-bromo-galactose. The mixture was stirred for about 14 hours. Then, 7 ml of Potassium hydroxide solution (1.25 mol/l) were added, followed by 15 ml of Aceto-bromo-galactoside (0.6 mol/l) in Acetone. The premixture was stirred for a further ten hours. The Ether and the Acetone were evaporated off at low pressure and the pH was adjusted to about 5.5 using glacial Acetic acid. The mixture containing some unreacted Alizarin was filtered and then washed in water before being dried overnight at 50° C.

The product was dried and dissolved in 200 ml of Dichloromethane before the addition of 2 ml of Triethylamine. An Aluminum oxide was premixed into the solution until thin layer chromatography (TLC) of test samples showed that no Alizarin remained. The Aluminum oxide was removed and the remaining solution was evaporated with rotary motion, yielding a yellow solid. This solid was recrystallized from hot Ethanol which contained a few drops of Acetic acid. This gave 1.96 g of Alizarin Tetra-acetyl-galactoside.

A mass of 1.1 g of Alizarin Tetra-acetyl-galactoside was resuspended in 60 ml of Ethanol before the addition of 30 ml of aqueous Sodium hydroxide (0.125 mol/l) to give a red solution. This mixture was kept at 65° C. for 10 minutes and then cooled to 0° C. The red glycosylated Alizarin Sodium salt was then removed by vacuum filtration, washed with Ether and finally dried. The procedure yielded 0.86 g of the Sodium salt of Alizarin-2-β-D-galactoside in the form of a crystalline, red powder.

3°) Synthesis of Alizarin-2-acetate

This substrate was prepared using a method familiar to those skilled in the art. Two grams of Alizarin were dissolved in 5 ml of Pyridine and treated with a mixture of 2.5 ml of Acetic anhydride and 5 ml of Pyridine. After 16 hours at room temperature, the yellow solution was poured into 100 ml of hydrochloric acid containing ice. The precipitated Acetate was recovered by filtration with aspiration and then washed in water. Recrystallization from Acetone yielded 1.4 g of Alizarin-2-acetate in the form of yellow crystals.

4°) Synthesis of Alizarin-2-sulfate

This substrate was prepared by heating 2.4 g of Alizarin (i.e. 10 mmol) in 10 ml of pyridine containing 4 g of a Pyridine-Sulfur trioxide complex. After 2 hours at 60° C., the Pyridine was removed at low pressure. The sulfate ester was recrystallized in the same way as the Potassium salt, by careful addition of Potassium hydroxide in methanol until a pH of 9 was reached. The Potassium salt forms gradually and was recovered by filtration with aspiration before being washed in Ether to yield 1.2 g of a white crystalline powder, Alizarin-2-sulfate.

5°) Synthesis of Alizarin-1-galactoside

This substrate was prepared from the Alizarin-2-acetate (the synthesis of which was described in Chapter 3°). A mass of 2,82 g of the ester (i.e. 10 mmol) was mixed into 75 ml of Dichloromethane and to this mixture was added 2 to 3 ml of either 2,4,6-Collidine or 2,6-Lutidine to generate a deep purple solution. After one hour, silver carbonate—prepared according to the method of Wolfrom and Lineback, "Methods in Carbohydrate Chemistry 2" (1963), 342–43—was added followed by 5 g (i.e. 12.5 mmol) of Aceto-bromo-galactose. The reaction is allowed to proceed at room temperature (i.e. 10 to 15° C.) for two days in a constantly stirred vessel. Thin layer chromatography revealed that steady conversion to Tetra-acetyl-galactoside (which migrates fast on the plate) was occurring. The solution was filtered through a Silica or a Diatomite bed and the filter aid was washed using sufficient (i.e. about 100 ml) Dichloromethane. The solution of the compound in Dichloromethane was then washed in 0.2 M hydrochloric acid (3×100 ml) in water (×2). After drying (MgSO$_4$), the light brown-colored extract was evaporated at low pressure and then dissolved in a new aliquot of methanol. Thin layer chromatography (Ethyl acetate/Toluene) revealed the presenbce of a fast-migrating species which gave a positive signal with ultraviolet radiation and sulfuric acid. The protected galactoside was then deacetylated—using Sodium methoxide in Methanol as already described—yielding 1.32 g of Alizarin-1-galactoside.

6°) Synthesis of Alizarin-1-phosphate-2-octanoate

This substrate was prepared by reacting 2.4 g (i.e. 10 mmol) in 100 ml of Dichloromethane and 3 ml of Triethylamine. To this solution, 1.62 g of Octanoyl chloride (10 mmol) was slowly added over a period of 30 minutes at room temperature, stirring throughout. The Octanoate was purified by treating it with Aluminum, as has already been described, and then recovered by removing the solvent and recrystallizing the product from Methanol. After cooling to −12° C., a mass of 1.84 g of the Octanoate (5 mmol) in 30 ml of dry Acetonitrile was successively treated with:

3.6 g of carbon tetrachloride,
1.6 g of Diisopropylethylamine, and
80 mg of 4-dimethylaminopyridine.

After about 2 minutes at low temperature, a solution containing 2.2 g of Dibenzyl phosphite was added in 8 ml of Acetonitrile which prevents the temperature rising too high. After one hour, the mixture was treated as described by Silverberg L. J., Dillon J. L. et Vermeshetti P., Tet. Lett., 37 N°6 (1996), and the dibenzyl-phosphoryl ester was destroyed using Hydrogen by using 30 ml of Ethyl acetate as solvent, in the presence of 0.4 g of a Palladium/Carbon catalyst (10% w/w). The Phosphate ester was then recovered in the same way as the Potassium salt, following removal of the acetate by mixing the solution with Methanol and then carefully adding a solution of Potassium carbonate in aqueous Methanol with a pH of 8. The precipitated Potassium salt of Alizarin-1-phosphoric acid-2-octanoate was recovered, washed in Methanol, and the 2.05 g of the Ester were vacuum dried and used without any further purification.

7°) Synthesis of Deoxyalizarin

This type of substrate is prepared following the pathway given by Liebermann—Ber., 21 444 (1888). To synthesize 9- and 10-O-Methyl derivatives of reduced Anthraquinones, all the 1,2-diol groups are first protected with methyl groups using the appropriate procedure (which is familiar to those skilled in the art) which consists in forming a complex with borate, as described in Scheline—Acta. Chem. Scand. 20 1182 (1966), or by using Acetaldehyde di-methyl acetate (protection by Ethylidene).

APPLICATIONS

Many applications are possible:
1. Detection and identification of particular microbial species in semi-solid media or on membranes.
2. Detection of enzyme activities in solutions containing extracts derived from tissues or cells, or in suspensions of eukaryotic or prokaryotic cells.
3. Identification of organisms on the basis of the enzyme activities that they express.
4. Visualization and localization of a specific reaction between an antigen and an antibody, as in ELISA methods. For example, Alizarin-β-galactoside or Alizarin-phosphate can be used for methods designed to detect β-galactosidase or alkaline phosphatase activities in assays for marker enzymes. In this case, the enzyme substrates are first used in detection reactions in which an enzyme activity (notably those of alkaline phosphatase or β-galactosidase) is involved, as for reactions designed to detect antibodies or antigens in an ELISA-type format, e.g. "Immunoassays: from Theory to Practice" edited by Y. Barbier and published by ACOMEN, Lyon, pages 109 to 133 (1988); or otherwise, in the detection of nucleic acids, e.g. "DNA probes" $2^{nd}$ Edition, Keller G. H., Manak, M. M., Stockton press, sections 5 to 9 (1993).
1. Techniques of molecular biology designed to detect the presence of a gene, e.g. that encoding β-galactosidase and its use "Molecular cloning: a laboratory manual" $2^{nd}$ Edition, Sambrook, Fritsch, Maniatis, Cold Spring Harbor Laboratory Press, sections 16.56 and section 1.85 (1989).
2. Techniques of histochemistry, cytochemistry and flow cytometry. The uses of such enzyme-specific substrates which are important in applications in medical diagnosis and other fields, e.g. water quality testing, environmental testing, the food industry, etc.

3. Detection of enzymes on polyacrylamide gels or other materials used for electrophoresis and other separation methods.

EXAMPLES

Example 1

Effect of Alizarin-2-β-D-galactoside Concentration on the Detection of β-galactosidase Activity Due to Microorganisms in a Semi-solid Medium A Columbia-base medium (46.37 g/l) was supplemented with either Alizarin-2-β-D-galactoside (0,01 g/l), 0,03 g/l, 0,05 g/l et 0,08 g/l) with Ammoniacal Iron Citrate (0,05 g/l), or with 6-Chloro-3-indoyl-β-D-galactoside (0,2 g/l) without any Ammoniacal Iron Citrate Petri dishes were prepared using these four different media (20 ml of medium per dish). These dishes were divided into three areas and then each area was inoculated with a bacterial suspension (density=0.5 McFarland). The dishes were incubated for 48 hours at 37° C. The colonies which grew were examined by eye after 18, 24 and 48 hours of incubation. Both the color and the intensity of the color were recorded. The results are presented in Table 1 below.

Example 2

Detection of β-galactosidase Activity Due to Microorganisms on a Semi-solid Medium—Use of Alizarin-2-β-D-galactoside Semi-solid medium supplemented with Alizarin-2-β-D-galactoside was prepared as follows: 46.37 g of Columbia agar were added to 1 liter of distilled water together with 50 mg of Alizarin-2–13-D-galactoside, 500 mg of Ammoniacal iron citrate and 30 mg of Isopropyl-β-D-thiogalactoside to induce β-galactosidase activity. The medium was sterilized by autoclaving at 116° C. for 10 minutes. It was then slowly cooled to 55° C. at which temperature it was poured into 20 ml Petri dishes. This medium was compared with another semi-solid medium prepared in the same way using 46.37 g of Columbia agar together with 80 mg of 5-Bromo-4-chloro-3-indolyl-β-D-galactoside and 30 mg of Isopropyl-β-D-thiogalactoside.

Three-hundred-and-sixty-seven (367) different strains collected from clinical and environmental specimens were identified using 20E API (Registered Trademark) strips (bioMérieux, France) as the reference method. All strains were grown on Columbia agar at 37° C. for 24 hours and then an inoculum of about $10^8$ organisms/ml (equivalent to a McFarland reading of 0,5) was prepared for every strain. Using a Denley inoculator, one dish of each of the media was inoculated with 1 microliter of each suspension, i.e.

TABLE 1

Effect of substrate concentration on the detection of β-galactosidase activity due to microorganisms in a semi-solid medium

| Strain | Incubation time | 6-Chloro-3-indolyl-β-D-galactoside 0.2 g/l | | Alizarine-2-β-D-galactoside 0.01 g/l | | Alizarin-2-β-D-galactoside 0.03 g/l | | Alizarin-2-β-D-galactoside 0.05 g/l | | Alizarin-2-β-D-galactoside 0.08 g/l | |
|---|---|---|---|---|---|---|---|---|---|---|---|
| | | Color | Intensity | Color | Intensity | Color | Intensity | Color | Intensity | Color | Intensity |
| Escherichia coli 115 | 18 H | pink | 3.5 | purple | 0.3 | purple | 2.7 | purple | 3.5 | purple | 4 |
| | 24 H | pink | 3.5 | purple | 0.3 | purple | 2.7 | purple | 3.5 | purple | 4 |
| | 48 H | pink | 3.5 | purple | 0.5 | purple | 3 | purple | 3.5 | purple | 4 |
| Klebsiella pneumoniae 023 | 18 H | — | — | — | — | purple | 0.3 | purple | 0.8 | purple | 1.5 |
| | 24 H | — | — | — | — | purple | 0.3 | purple | 1 | purple | 1.5 |
| | 48 H | pink | 0.3 | — | — | purple | 0.5 | purple | 1 | purple | 1.7 |
| Enterococcus faecalis 117 | 18 H | — | — | purple | 0.3 | purple | 2.7 | purple | 4 | purple | 4 |
| | 24 H | — | — | purple | 0.6 | purple | 3 | purple | 4 | purple | 4 |
| | 48 H | — | — | purple | 0.6 | purple | 3.5 | purple | 4 | purple | 4 |
| Serratia marcescens 042 | 18 H | pink | 0.3 | — | — | purple | 0.5 | purple | 1 | purple | 2 |
| | 24 H | pink | 0.8 | — | — | purple | 1 | purple | 2.5 | purple | 2.5 |
| | 48 H | pink | 3.5 | purple | 0.3 | purple | 1.7 | purple | 3 | purple | 3.5 |
| Proteus vulgaris 087 | 18 H | — | — | — | — | — | — | — | — | — | — |
| | 24 H | — | — | — | — | — | — | — | — | — | — |
| | 48 H | — | — | — | — | — | — | — | — | — | — |
| Morganella morganii 060 | 18 H | — | — | — | — | — | — | — | — | — | — |
| | 24 H | — | — | — | — | — | — | — | — | — | — |
| | 48 H | — | — | — | — | — | — | — | — | — | — |

In Table 1, the sign "–" signifies no coloration. The strains which gave nothing but negative results are used as negative controls.

From Table 1, it can be seen that Alizarin-2-β-D-galactoside at a concentration of 0.03 g/l gives an intensity of color very close to that observed with 6-Chloro-3-indolyl-β-D-galactoside at a concentration which is about seven times higher. The range of concentrations at which Alizarin-2-β-D-galactoside gives useful intensities of color is between 0.03 g/l et 0.08 g/l, preferably 0.05 g/l. Alizarin-based substrates are therefore more sensitive than Indoxyl-based ones.

both the medium supplemented with Alizarin-2-β-D-galactoside prepared as described above, and the medium containing 5-Bromo-4-chloro-3-indolyl-β-D-galactoside. All the dishes were incubated for 18 hours at 37° C.

After incubation, the colonies which had grown were inspected by eye. On the medium containing the Alizarin-2-β-D-galactoside, the colonies expressing β-galactosidase activity were purple in color whereas on the medium containing the 5-Bromo -4-chloro-3-indolyl-β-D-galactoside, they were turquoise. Any strain showing either of these colors was considered as being positive for β-galactosidase with the corresponding substrate. The results are presented in Table 2 below.

TABLE 2

Detection of β-galactosidase activity due to microorganisms on a semi-solid medium supplemented with Alizarin-2-β-D-galactoside

| Species | Number of strains tested per species | Alizarin-2-β-D-galactoside | 5-Bromo-4-chloro-3-indolyl-2-β-D-galactoside |
|---|---|---|---|
| *Acinetobacter* spp. | 53 | 0 | 0 |
| *Aeromonas caviae* | 7 | 86 | 86 |
| *Aeromonas hydrophila* | 3 | 100 | 100 |
| *Citrobacter diversus* | 9 | 89 | 89 |
| *Citrobacter freundii* | 16 | 100 | 100 |
| *Enterobacter aerogenes* | 9 | 100 | 100 |
| *Enterobacter agglomerans* | 1 | 100 | 100 |
| *Enterobacter cloacae* | 21 | 100 | 100 |
| *Escherichia coli* | 41 | 95 | 95 |
| *Escherichia hermannii* | 1 | 100 | 100 |
| *Hafnia alvei* | 10 | 80 | 80 |
| *Klebsiella oxytoca* | 13 | 100 | 100 |
| *Klebsiella ozaenae* | 3 | 100 | 67 |
| *Klebsiella pneumoniae* | 19 | 100 | 100 |
| *Morganella morganii* | 12 | 0 | 0 |
| *Proteus mirabilis* | 16 | 0 | 0 |
| *Proteus penneri* | 1 | 0 | 0 |
| *Proteus vulgaris* | 4 | 0 | 0 |
| *Providencia alcalifaciens* | 3 | 0 | 0 |
| *Providencia rettgeri* | 3 | 0 | 0 |
| *Providencia stuartii* | 10 | 0 | 0 |
| *Salmonella* spp. | 64 | 0 | 0 |
| *Serratia odorifera* | 1 | 100 | 100 |
| *Serratia* spp. | 14 | 86 | 79 |
| *Shigella boydii* | 1 | 0 | 0 |
| *Shigella dysenteriae* | 2 | 0 | 0 |
| *Shigella flexneri* | 2 | 0 | 0 |
| *Shigella sonnei* | 10 | 100 | 100 |
| *Vibrio cholerae* | 1 | 100 | 100 |
| *Yersinia enterocolitica* | 14 | 64 | 29 |
| *Yersinia pseudotuberculosis* | 3 | 67 | 0 |

The figures given in the Alizarin-2-β-D-galactoside and 5-Bromo-4-chloro-3-indolyl-β-D-galactoside columns correspond to the percentage of positive strains. The vast majority of strains (96.5%) reacted in exactly the same way—i.e. either positively or negatively—with both substrates. Eight strains selectively hydrolyzed Alizarin-2-β-D-galactoside. Nevertheless, all eight of these strains possessed β-galactosidase activity as shown by the production of a fluorescent signal in the presence of the substrate 4-Methylumbelliferyl-β-D-galactoside. The results in this Table therefore show that the substrate is an effective marker for β-galactosidase activity with a greater sensitivity than that observed with the reference substrate, 5-Bromo-4-chloro-3-indolyl-β-D-galactoside. Therefore, these substrates are extremely sensitive and can be used at very low concentrations.

Example 3

Effect of Using Different Metal Salts on the Color of the Marker Part

To the Columbia-base medium (46.37 g/l) supplemented with Alizarin-2-β-D-glucoside (50 mg/l), were added either Manganese chloride, Ammoniacal iron citrate, Tin chloride, or Aluminum sulfate, all at a concentration of 50 mg/l. A control medium with no metal salts was tested in parallel. After autoclaving, these various media were all used to prepare Petri dishes (20 ml per plate). These dishes were divided into three areas and then each area was inoculated with a suspension (density=0.5 McFarland) of microorganisms taken from the Applicant's collection. The dishes were incubated for 48 hours at 37° C. The colonies which grew were examined by eye after 24 and 48 hours of incubation. Both the color and the intensity of the color were recorded. The results are presented in Table 3 below. It should be pointed out that intensity readings are in arbitrary units. The only purpose of giving these values is to make it possible to compare one strain with another in this respect. The same is true for the examples which follow. Similarly, the strains tested were taken from the Applicant's collection and the number given represents an internal reference specific to this collection. The same internal numbering system is also used in some of the examples given later on.

TABLE 3

Effect of using different metal salts on the color of the marker part

| Strain | Incubation time | Control | | Manganese chloride | | Iron citrate | | Tin chloride | | Aluminium sulfate | |
|---|---|---|---|---|---|---|---|---|---|---|---|
| | | Color | Intensity | Color | Intensity | Color | Intensity | Color | Intensity | Color | Intensity |
| *Listeria monocytogenes* 023 | 24 H | purple | 2 | purple | 2.7 | purple | 4 | orange | 3 | red | 4 |
| | 48 H | purple | 2 | purple | 2.7 | purple | 4 | orange | 4 | red | 4 |

TABLE 3-continued

Effect of using different metal salts on the color of the marker part

| Strain | Incubation time | Control | | Manganese chloride | | Iron citrate | | Tin chloride | | Aluminium sulfate | |
|---|---|---|---|---|---|---|---|---|---|---|---|
| | | Color | Intensity | Color | Intensity | Color | Intensity | Color | Intensity | Color | Intensity |
| Listeria monocytogenes 079 | 24 H | purple | 2.3 | purple | 2.7 | purple | 4 | orange | 3.5 | red | 4 |
| | 48 H | purple | 2.3 | purple | 2.7 | purple | 4 | orange | 4 | red | 4 |
| Listeria monocytogenes 081 | 24 H | purple | 2.3 | purple | 2.3 | purple | 4 | orange | 3 | red | 4 |
| | 48 H | purple | 2.3 | purple | 2.7 | purple | 4 | orange | 4 | red | 4 |
| Listeria ivanovii 018 | 24 H | purple | 2.3 | purple | 2.7 | purple | 4 | orange | 3 | red | A |
| | 48 H | purple | 2.3 | purple | 2.7 | purple | 4 | orange | 4 | red | 4 |
| Listeria ivanovii 020 | 24 H | purple | 2.3 | purple | 2.7 | purple | 4 | orange | 3 | red | 4 |
| | 48 H | purple | 2.3 | purple | 2.7 | purple | 4 | orange | 4 | red | 4 |
| Listeria ivanovii 032 | 24 H | purple | 2.3 | purple | 2.3 | purple | 4 | orange | 3 | red | 4 |
| | 48 H | purple | 2.3 | purple | 2.3 | purple | 4 | orange | 4 | red | 4 |
| Listeria innocua 036 | 24 H | purple | 2.3 | purple | 2.3 | purple | 4 | orange | 3 | red | 4 |
| | 48 H | purple | 2.7 | purple | 2.7 | purple | 4 | orange | 4 | red | 4 |
| Listeria innocua 029 | 24 H | purple | 2 | purple | 2.3 | purple | 4 | orange | 3 | red | 4 |
| | 48 H | purple | 2.3 | purple | 2.3 | purple | 4 | orange | 4 | red | 4 |
| Listeria innocua 077 | 24 H | purple | 2.3 | purple | 2.3 | purple | 4 | orange | 3 | red | 4 |
| | 48 H | purple | 2.3 | purple | 2.3 | purple | 4 | orange | 4 | red | 4 |
| Listeria seeligeri 011 | 24 H | purple | 2.3 | purple | 2.7 | purple | 4 | orange | 3 | red | 4 |
| | 48 H | purple | 2.3 | purple | 2.7 | purple | 4 | orange | 4 | red | 4 |
| Listeria welshimeri 023 | 24 H | purple | 2.3 | purple | 2.3 | purple | 4 | orange | 3 | red | 4 |
| | 48 H | purple | 2.3 | purple | 2.7 | purple | 4 | orange | 4 | red | 4 |
| Listeria grayi 078 | 24 H | purple | 2 | purple | 2 | purple | 4 | orange | 3 | red | 4 |
| | 48 H | purple | 2.3 | purple | 2 | purple | 4 | orange | 4 | red | 4 |

The color observed following hydrolysis of the substrate varies according to the metal salt used. Color can even be observed in the absence of any metal salts (i.e. in the control medium). However, the color is less intense than that seen in the presence of a metal salt, e.g. the Iron salt (which does not affect the actual color).

This means that both the color and its intensity can be varied to match specific requirements (e.g. when used in combination with other enzyme substrates or a pH indicator).

Example 4

Effect of pH on β-D-galactosidase Detection in the Presence of Alizarin-2-β-D-galactoside To each of eighteen tubes containing 5 ml of osmotically purified water, the following were added Alizarin-2-β-D-galactoside (0.05 g/l) and 5 µl of 62 -galactosidase (EC 3.2.1.23 Sigma). Ammoniacal iron citrate (0.05 g/l) was added to half of these tubes. All 18 tubes were incubated for 4 hours at 37° C., after which the tubes which did not contain any Ammoniacal iron citrate had a light pink color, whereas the pink coloration in those which had been supplemented with Ammoniacal iron citrate was observed to be more intense. Finally, the pH of these tubes was adjusted to different values (2–3–4–5–6–7–8–9–10) at 24° C. The colors observed at the different PH readings are presented in Table 4 below.

TABLE 4

Effect of pH on β-D-galactosidase detection in the presence of 2-Alizarin-β-D-galactoside.

| pH | Tubes containing no iron | Tubes supplemented with iron |
|---|---|---|
| pH 2 | Yellow | Yellow |
| pH 3 | Yellow | Yellow |
| pH 4 | Yellow | Yellow |
| pH 5 | Yellow - Orange | Yellow - Pink |
| pH 6 | Pink - Orange | Pink |
| pH 7 | Pink - Orange | Pink |
| pH 8 | Pink | Purple |
| pH 9 | Purple | Purple |
| pH 10 | Mauve | Mauve |

The color changes with pH. As a general rule, at low pH it is yellow, and at higher pH it is pink or purple. This means that the color can be varied to suit requirements or to detect different metabolic parameters (e.g. enzyme hydrolysis and pH variations). This experiment also shows that a wide range of different pH values can be used.

Example 5

Combining an Alizarin-based Substrate with Another Substrate in a Semi-solid Medium-detection of at Least Two Different Enzyme Activities The following medium:

Columbia base (46.37 g/l),

Alizarin-2-β-D-glucoside (0,05 g/l),

Ammoniacal iron citrate (0.05 g/l),

5-Bromo-4-chloro-3-indolyl-β-D-galactoside (0,05 g/l), and

Isopropyl-β-D-thiogalactoside (30 mg/l) to induce β-galactosidase activity, was used to pour Petri dishes (30 ml per plate). These dishes were divided into three areas and then each area was inoculated with a suspension (density=0.5 McFarland) of microorganisms taken from the Applicant's collection. The dishes were incubated for 48 hours at 37° C.

The colonies which grew were examined by eye after 24 and 48 hours of incubation. Both the color and the intensity of the color were recorded. The results are presented in Table 5 below.

TABLE 5

Simultaneous testing of two substrates: Alizarin-2-β-D-glucoside and 5-Bromo-4-chloro-3-indolyl-β-D-galactoside

| Strain | Incubation time | Alizarin-2-β-Glucoside plus 5-Bromo-4-chloro-3-indolyl-β-D-galactoside | |
|---|---|---|---|
| | | Color | Intensity |
| Escherichia coli 115 | 24 H | Turquoise | 3.5 |
| | 48 H | Turquoise | 4 |
| Escherichia coli 206 | 24 H | Turquoise | 3.5 |
| | 48 H | Turquoise | 4 |
| Citrobacter freundii 136 | 24 H | Turquoise | 3.5 |
| | 48 H | Turquoise | 3.5 |
| Enterococcus faecalis 117 | 24 H | Purple | 4 |
| | 48 H | Purple | 4 |
| Enterococcus faecalis 066 | 24 H | Purple | 4 |
| | 48 H | Purple | 4 |
| Enterococcus faecium 039 | 24 H | Purple | 4 |
| | 48 H | Purple | 4 |
| Klebsiella pneumoniae 023 | 24 H | Blue Mauve | 4 |
| | 48 H | Blue Mauve | 4 |
| Enterobacter cloaecae 059 | 24 H | Blue Mauve | 4 |
| | 48 H | Blue Mauve | 4 |
| Citrobacter koseri 002 | 24 H | Blue Mauve | 4 |
| | 48 H | Blue Mauve | 4 |
| Morganella morganii 035 | 24 H | — | — |
| | 48 H | — | — |
| Pseudomonas aeruginosa 054 | 24 H | — | — |
| | 48 H | — | — |
| Proteu mirabilis 154 | 248 H | — | — |
| | 48 H | — | — |

In Table 5, the sign "–" signifies no coloration. The strains which gave nothing but negative results are used as negative controls.

By using a combination of two different substrates, four different groups of microorganism can be distinguished:
- the first group, members of which give a turquoise color, corresponds to species which express only β-galactosidase activity,
- the second group, members of which give a purple color, corresponds to species which express only β-glucosidase activity,
- members of the third group show a hybrid of the two patterns above, namely a blue or mauve color, and correspond to species which express both of the enzyme activities being assayed, and
- the fourth, colorless group corresponds to species which express neither of the above-mentioned activities.

It is therefore possible, using Alizarin-based substrates combined with other enzyme substrates, to distinguish between one or more groups of micro-organisms on the basis of the biochemical activities that they express.

Example 6

Detection of β-glucosidase Activity Due to Microorganisms on a Semi-solid Medium—Use of Alizarin-2-β-D-glucoside Into a well of an API (Registered trademark, bioMérieux, France) strip, 3 μl of a mixture of Alizarin-2-β-D-glucoside (0.12 g/l) and Ammoniacal iron citrate (0.05 g/l) were introduced and then dried. A control well containing a final concentration of 0.4 g/l of 6-Chloro-3-indolyl-β-D-glucoside was set up in parallel. Then 50 μl of Columbia base were added to both of these wells which were subsequently inoculated with 100 μl of a bacterial suspension (density=2 McFarland). After 4 and 24 hours of incubation at 37° C., the color generated in the wells was recorded. The results are presented in Table 6 below.

TABLE 6

Detection of β-glucosidase activity due to microorganisms on a semi-solid medium supplemented with Alizarin-2-β-D-glucoside

| Strain | Incubation time | Color observed with the Alizarin-2-β-D-glucoside | Color observed with the 6-Chloro-3-indolyl-β-D-glucoside |
|---|---|---|---|
| Listeria monocytogenes 022 | 4 H | Purple | Pink |
| | 24 H | Purple | Pink |

TABLE 6-continued

Detection of β-glucosidase activity due to microorganisms on a semi-solid medium supplemented with Alizarin-2-β-D-glucoside

| Strain | Incubation time | Color observed with the Alizarin-2-β-D-glucoside | Color observed with the 6-Chloro-3-indolyl-β-D-glucoside |
|---|---|---|---|
| *Listeria ivanovit* | 4 H | Purple | Pink |
| 018 | 24 H | Purple | Pink |
| *Listeria innocua* | 4 H | Purple | Pink |
| 036 | 24 H | Purple | Pink |
| *Listeria seeligeri* | 4 H | Purple | — |
| 080 | 24 H | Purple | Pink |
| *Bacillus thuringiensis* | 4 H | — | — |
| 072 | 24 H | Purple | — |
| *Klebsiella pneumoniae* | 4 H | Purple | Pink |
| 023 | 24 H | Purple | Pink |
| *Staphylococcus aureus* | 4 H | — | — |
| 062 | 24 H | — | — |
| *Enterococcus faecium* | 4 H | Purple | Pink |
| 009 | 24 H | Purple | Pink |

In Table 6, the sign "–" signifies no coloration. The strains which gave nothing but negative results are used as negative controls.

The Alizarin-based substrate detected activity in seven (7) of the eight (8) species tested, whereas 6-Chloro-3-indolyl-β-D-glucoside only detected such activity in 6) of these species. Moreover, in the case of two of these species (*Bacillus thuringiensis* and *Listeria seeligeri*), their activity manifested at an earlier time point with the Alizarin-based substrate. Therefore, these substrates can not only be used in liquid broth, but they are also more sensitive than Indoxyl-based substrates.

Example 7

Comparison of Alizarin-1-β-D-glucoside and Alizarin-2-β-D-glucoside in Semi-solid Medium To Columbia base, were added, either:

Alizarin-2-β-D-glucoside at 0.05 g/l plus Ammoniacal iron citrate at 0.05 g/l,

Alizarin-1-β-D-glucoside at 0.05 g/l and 0.1 g/l plus, for both concentrations, Ammoniacal iron citrate at 0.05 g/l, 6-Chloro-3-indolyl-β-D-glucoside at 0.15 g/l without any Ammoniacal iron citrate.

Petri dishes were prepared using these four media (20 ml of medium per dish). These dishes were divided into three areas and then each area was inoculated with a bacterial suspension (density=0.5 McFarland). The dishes were incubated for 48 hours at 37° C. The colonies which grew were examined by eye after 18, 24 and 48 hours of incubation. Both the color and the intensity of the color of the colonies were recorded. The results are presented in Table 7 below.

TABLE 7

Comparison of Alizarin-1-β-D-glucoside and Alizarin-2-β-D-glucoside in semi-solid medium.

| Strain | Incubation time | 6-Chloro-3-indolyl-β-D-glucoside | | 2-Alizarin-β-D-glucoside | | 1-Alizarin1-β-D-glucoside (0.05 g/l), | | 1-Alizarin1-β-D-glucoside (0.1 g/l), | |
|---|---|---|---|---|---|---|---|---|---|
| | | Color | Intensity | Color | Intensity | Color | Intensity | Color | Intensity |
| *Escherichia coli* | 18 H | — | — | — | — | — | — | — | — |
| 115 | 24 H | — | — | — | — | — | — | — | — |
| | 48 H | — | — | — | — | — | — | — | — |
| *Citrobacter koseri* | 18 H | Pink | 0.5 | Mauve | 2 | Mauve | 1.5 | Mauve | 2.5 |
| 059 | 24 H | Pink | 1 | Mauve | 3 | Mauve | 2 | Mauve | 3 |
| | 48 H | Pink | 2 | Mauve | 3.5 | Mauve | 2.5 | Mauve | 4 |
| *Enterococcus faecalis* | 18 H | Pink | 1.5 | Purple | 3.5 | Purple | 3.5 | Purple | 3.5 |
| 117 | 24 H | Pink | 2 | Purple | 4 | Purple | 4 | Purple | 4 |
| | 48 H | Pink | 2.5 | Purple | 4 | Purple | 4 | Purple | 4 |
| *Klebsiella* | 18 H | Pink | 2 | Purple | 3.5 | Purple | 2.5 | Purple | 3.5 |
| *pneumoniae* | 24 H | Pink | 2.5 | Purple | 4 | Purple | 3 | Purple | 4 |
| 023 | 48 H | Pink | 3 | Purple | 4 | Purple | 3.5 | Purple | 4 |
| *Proteus mirabilis* | 18 H | — | — | — | — | — | — | — | — |
| 008 | 24 H | — | — | — | — | — | — | — | — |
| | 48 H | — | — | — | — | — | — | — | — |
| *Staphylococcus* | 18 H | — | — | — | — | — | — | — | — |
| *epidermidis* | 24 H | — | — | — | — | — | — | — | — |
| 024 | 48 H | — | — | — | — | — | — | — | — |

In Table 7, the sign "–" signifies no coloration. The strains which gave nothing but negative results are used as negative controls.

At an equivalent concentration of 0.05 g/l, the two substrates did not give the same intensity of color with two (2) of the three (3) strains which expressed the activity. The Alizarin-2-β-D-glucoside is slightly more sensitive than the Alizarin-1-β-D-glucoside. However, at a concentration of 0.1 g/l, Alizarin-1-β-D-glucoside gave deeper intensities than Alizarin-2-β-D-glucoside.

From this Table, it can be seen that the intensities observed with Alizarin-1-β-D-glucoside at a concentration of 0.05 g/l were-for all strains tested-deeper than those obtained with 6-Chloro-3-indolyl-β-D-glucoside which was at a three-fold higher concentration.

Alizarin-based substrates are therefore more sensitive than Indoxyl-based ones.

The choice of whether to use Alizarin-1-β-D-glucoside or Alizarin-2-β-D-glucoside might be affected by other factors, such as production cost, stability, particulars of the application, etc.

SPECIAL POINTS

One method of visualizing and therefore identifying bacterial species in colonies involves growing them on a semi-solid medium supplemented with at least one substrate as synthesized above in the presence of trace quantities of at least one appropriate cation. The growing colonies thus take on an intense coloration (red, purple, blue, etc.) which depends on the substrate used, and the cation associated with it. When a ratio exists between the substrate and the cation, it is between 1/100 and 100/1, preferably between 1/10 and 10/1, and more preferably still, between 1/2 and 2/1.

In certain conditions, the presence of a $SO_3H$ group at position $R_3$ of the substrate helps overcome problems of stability and solubility associated with this type of substrate.

The term "polyvalent cations" refers to multivalent metal cations of the $X^{n+}$ type, with n=2, 3 or 4. The metals which can be used are: Mg, Al, Ca, Ti, V, Cr, Mn, Fe, Co, Ni, Cu, Zn, Sr, Zr, Sn, Sb, Ba, La and Hf, as well as the Lanthanides Ce, Sm, Eu, Gd and Tb.

The Anthrarobins (also referred to as Deoxyalizarin or Anthracene-1,2,10-triol) which are produced by the reduction of Alizarin, are already familiar to those skilled in the art. Reduction is mediated by the action of Zinc hydroxide, ammonia, Acid tin chloride, etc. This compound's general formula is as follows:

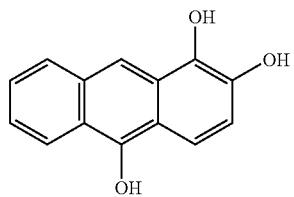

Because of the absence of the central quinonoid ring of Anthraquinone, the reactivity of metal chelation complexes of the 1,2-diol system is different, e.g. the ferrous chelation complex is black in color. Since Alizarin ferrous chelation complexes are red, two different types of substrate—to detect two different enzyme activities—can be used with the same metal ion. This pair of substrates could be, for example:

Alizarin-2-β-D-glucoside to detect saccharidase activity, and

Deoxyalizarin-2-β-D-phosphatase to detect phosphatase activity.

It is also possible to protect the hydroxyl group at position 10 of the Anthrarobins in which—for example—the hydrogen atom can be substituted by a methyl group giving a compound with the following structure:

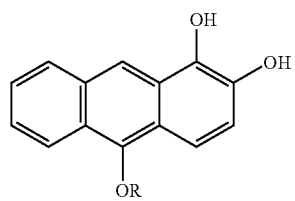

Similarly, the Alizarins can alsobe protected by reducing the ketone groups to generate a 9,10-diol structure; the alcohol groups can then be alkylated, e.g. to give 1,2-Dihydroxy-9,10-dimethoxyvanthracene, as represented in the following:

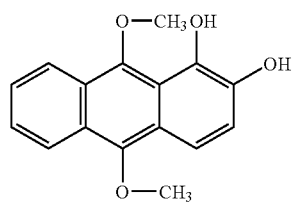

These alkylated Anthrarobins and Alizarins are not susceptible to spontaneous oxidization to form Alizarins and are, as a result, excellent candidates for the glycosidation of substrates, preferentially at position 2.

The invention claimed is:
1. A method for detecting enzyme activity comprising bringing at least one substrate, the target part of which matches the activity of the enzyme being assayed, into contact with a sample suspected of containing at least one microorganism which expresses said enzyme activity, and at least one type of cation, and
monitoring for the formation of an insoluble, colored chelation complex, wherein said substrate has following general formula:

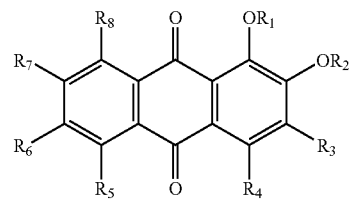

in which:
$R_1$ is a target part or H, and $R_2$ is a target part or H, with at least one of $R_1$ and $R_2$ being a target part,
$R_3$ is H, $SO_3H$, Cl, Br, F, I, $NO_2$, $NH_2$, $NR_9R_{10}$, or an acylamino, aminoaryl, or aminoacylamino group of the type NHCOX, with X being an alkyl, aryl or aralkyl group or an a-amino acid residue,
$R_4$ is H, $SO_3H$, Cl, Br, F, I, $NO_2$, $NH_2$, $NR_9R_{10}$, OH or an acylamino aminoaryl or aminoacylamino group of the type NHCOX, with X being an alkyl, aryl or aralkyl group or an a-amino acid residue, alternatively, $R_3$ and $R_4$ form bonds with one another to create a ring with at least five sides, $R_5$, $R_6$, $R_7$ and $R_8$ are each independently selected from the group consisting of H, a halogen, OH, $SO_3H$, an alkyl group and an alkoxy group, and $R_9$ and $R_{10}$ are independently an alkyl, aryl, aralkyl group, or either $R_9$ or $R_{10}$ is a ring structure with the other, either $R_{10}$ or $R_9$, being a hydrogen atom.

2. The method of claim 1, wherein the ketone groups of the central ring are reduced to form hydroxide groups in which at least one of the hydrogen atoms are optionally replaced by an alkyl group, aryl group or aralkyl group.

3. A method for detecting enzyme activity comprising

Bringing at least one substrate, the target part of which matches the activity of the enzyme being assayed, into contact with a sample suspected of containing at least one microorganism which expresses said enzyme activity, and at least one type of cation, and monitoring for the formation of an insoluble, colored chelation complex, wherein said substrate has the following general formula:

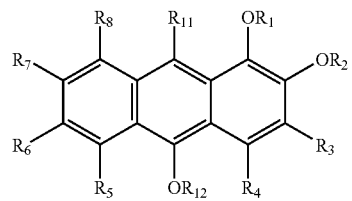

in which:

$R_1$ is a target part or H, and $R_2$ is a target part or H, with at least one of $R_1$ and $R_2$ being a target part, $R_3$ is H, $SO_3H$, Cl, Br, F, I, $NO_2$, $NH_2$, $NR_9R_{10}$, or an acylamino aminoaryl or aminoacylamino group of the type NHCOX, with X being an alkyl, aryl or aralkyl group or an a-amino acid residue, $R_4$ is H, $SO_3H$, Cl, Br, F, I, $NO_2$, $NH_2$, $NR_9R_{10}$, OH or an acylamino aminoaryl or aminoacylamino group of the type NHCOX, with X being an alkyl, aryl or aralkyl group or an a-amino acid residue, alternatively, $R_3$ and $R_4$ form bonds with one another to create a ring with at least five sides, $R_5$, $R_6$, $R_7$ and $R_8$ are each independently selected from the group consisting of H, a halogen, OH, $SO_3H$, an alkyl group and an alkoxy group, and $R_9$ and $R_{10}$ are independently an alkyl, aryl, aralkyl group, or one, either $R_9$ or $R_{10}$ is a ring structure with the other, either $R_{10}$ or $R_9$, being a hydrogen atom, $R_{11}$ is a member selected from the group consisting of H, $SO_3H$, Cl, Br, F, I, $NO_2$, $NH_2$, $NR_9R_{10}$, or an alkyl, aryl, aralkyl, acylamino aminoaryl or aminoacylamino group of the type NHCOX, with X being an alkyl, aryl or aralkyl group, and an a-amino acid residue, and $R_{12}$ is a member selected from the group consisting of H, an alkyl group, an aryl group and an aralkyl group.

4. The method of claim 1, wherein $R_1$ is H and $R_2$ is a target part.

5. The method of claim 1, wherein the target part is a member of the group consisting of:

a glycoside, consisting of mono-, di- or poly-saccharide sub-units, joined to the hydroxyl group through" α or β carbon, an "amino acid or a peptide", an organic acid having a formula —O—CO—$(CH_2)_n$—$CH_3$, in which n has a value of between 0 and 20, and sulfate, phosphate, pyrosulfate, pyrophosphate or phosphodiester.

6. The method of claim 1, wherein $R_3$ and $R_4$ are such that, when joined to one another through a substituted or unsubstituted $C_3N$ chain, a six-sided ring is formed.

7. The method of claim 1, wherein the substrate is introduced in the presence of at least one type of cation, wherein said cation is reactive for the colored chelation complex that is formed.

8. The method of claim 7, wherein said type of cation is a member selected from the group consisting of $Fe^{2+}$, $Al^{3+}$, $Mn^{2+}$, $Sn^{2+}$ and $Cu^{2+}$.

9. The method of claim 1, wherein at least two substrates are used to detect the presence of at least two different enzyme activities, wherein said method comprises the following steps:

bringing at least two substrates, the target parts of which match the activities of said at least two enzymes being assayed, into contact with a sample suspected of containing at least one microorganism which expresses the enzyme activities of the two enzymes, plus at least one type of cation, and monitoring for the development of at least two different colors or a third color.

10. The method of claim 9, wherein the substrate is introduced in the presence of at least one type of cation, wherein said cation is reactive for all the chelation complexes that are formed.

11. The method of claim 1, said method comprising:

bringing at least one substrate, the target part of which matches the activity of the enzyme being assayed, into contact with a sample suspected of containing at least one microorganism which expresses said enzyme activity, in a reaction medium with an appropriate pH, and monitoring for the development of at least one color.

12. The method of claim 1, wherein a single type of cation is reactive for all the chelation complexes that are formed.

13. The method of claim 1, further comprising growing the microorganism(s) on a culture medium supplemented with the substrate(s).

14. The method of claim 1, wherein glycosidase enzyme activity is detected, and the target part is selected from the group consisting of glucose, galactose, mannose, xylose, glucuronic acid and N-acetylglucosamine.

* * * * *

UNITED STATES PATENT AND TRADEMARK OFFICE
CERTIFICATE OF CORRECTION

PATENT NO. : 7,052,863 B2
APPLICATION NO. : 10/148600
DATED : May 30, 2006
INVENTOR(S) : Armstrong et al.

It is certified that error appears in the above-identified patent and that said Letters Patent is hereby corrected as shown below:

Column 23, Claim 1, line 2 - change "a-amino" to -- α-amino --

Column 23, Claim 3, line 16 - change "Bringing" to -- bringing --

Column 23, Claim 3, line 41 - change "a-amino" to -- α-amino --

Column 23, Claim 3, line 45 - change "a-amino" to -- α-amino --

Column 23, Claim 3, line 58 - change "a-amino" to -- α-amino --

Column 24, Claim 5, line 4 - change "through" α or" to -- through α or --

Column 24, Claim 5, line 10 - change "an "amino acid or a peptide"," to -- an amino acid or a peptide, --

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,052,863 B2 Page 1 of 1
APPLICATION NO. : 10/148600
DATED : May 30, 2006
INVENTOR(S) : Lyle Armstrong and Arthur James It is certified that error appears in the above-identified patent and that said Letters Patent is hereby corrected as shown below:

Column 22, line 67, change "acylamino aminoaryl" to --acylamino, aminoaryl--;
Column 23, line 39, change "acylamino aminoaryl" to --acylamino, aminoaryl--; and
Column 23, line 43, change "acylamino aminoaryl" to --acylamino, aminoaryl--.

Signed and Sealed this

Seventeenth Day of November, 2009

David J. Kappos
*Director of the United States Patent and Trademark Office*